United States Patent
Fujiyama et al.

[11] 3,957,969
[45] May 18, 1976

[54] COSMETIC STICK COMPRISING WATER-IN-OIL EMULSION

[75] Inventors: Yoshio Fujiyama, Yokohama; Yoshihiro Kanda, Kiyose; Hajime Matsuda, Yokohama, all of Japan

[73] Assignee: Shiseido Co., Ltd., Tokyo, Japan

[22] Filed: July 13, 1973

[21] Appl. No.: 379,063

[52] U.S. Cl. ............................ 424/64; 424/361; 424/365; 424/DIG. 5
[51] Int. Cl.² ............................ A61K 7/025
[58] Field of Search .................... 424/64, DIG. 5

[56] References Cited
UNITED STATES PATENTS

| | | | |
|---|---|---|---|
| 1,320,855 | 11/1919 | Henderson | 424/DIG. 5 |
| 2,143,060 | 1/1939 | Dzialosohinsky | 424/DIG. 5 |
| 2,853,422 | 9/1958 | Jarrett | 424/64 |
| 2,889,253 | 6/1959 | Berger et al. | 424/DIG. 5 |
| 2,890,987 | 6/1959 | Hilfer | 424/DIG. 5 |
| 3,148,125 | 9/1964 | Strianse et al. | 424/DIG. 5 |
| 3,279,999 | 10/1966 | Harrison et al. | 424/DIG. 5 |
| 3,489,690 | 1/1970 | Lachampt et al. | 424/64 |
| 3,642,980 | 2/1972 | Lachampt et al. | 424/64 |
| 3,745,033 | 7/1973 | Hutchison | 424/64 |

*Primary Examiner*—Leonard Schenkman
*Attorney, Agent, or Firm*—Paul & Paul

[57] ABSTRACT

A cosmetic stick having an excellent spreading property on human skin is prepared from a water-in-oil emulsion which comprises 1 to 50 weight % of water, 1 to 10 weight % of a polyhydroxy compound selected from glycerol, mannitol, dulcitol and carbohydrates, 1 to 5 weight % of an oleic acid esters of polyhydric alcohols and the balance consisting of a cosmetic base material.

14 Claims, 1 Drawing Figure

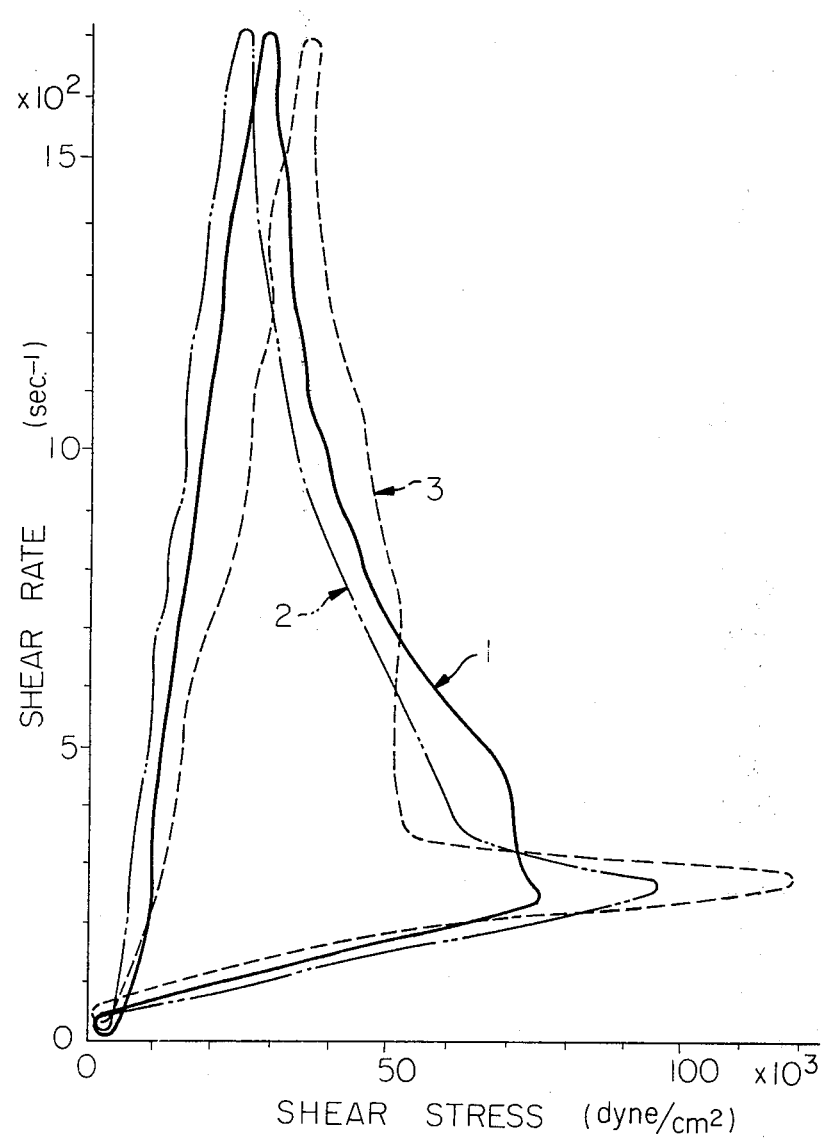

COSMETIC STICK COMPRISING WATER-IN-OIL EMULSION

The present invention relates to a stick-shaped cosmetic which may be readily spread on the skin. Particularly, the present invention relates to a cosmetic stick comprising a water-in-oil emulsion and having an excellent spreading property on the human skin.

Broadly speaking, the conventional cosmetic sticks such as lipstick, lip-pomade, stick foundation and cosmetic are all composed of, as a major component an oil-soluble material, for example, vegetable, animal and mineral oils, fats and waxes and higher carboxylic acid esters, and as a minor component, coloring material (dye and pigment), perfume and/or antioxidant. They are generally, hydrophobic. Therefore, it is very difficult to uniformly mix the above-mentioned materials with water. However, the cosmetics containing water therein are desirable to enhance compatibility of the cosmetics with the human skin.

Recently, water-in-oil emulsions for the preparation of cosmetic lotions and creams were developed, for example, in U.S. Pat. No. 3,536,816. However, the conventional water-in-oil emulsions result in various disadvantages when an attempt is made to use them in cosmetic sticks. Such disadvantages are, discoloring of the coloring material non-uniform mixing of the coloring material, undesirable softening, easy breaking, bleeding of oils and difficulty in molding. Because of the disadvantages stated above there is as yet no water-in-oil emulsion cosmetic stick.

The object of the present invention is to provide a cosmetic stick comprising a water-in-oil emulsion which is effective for improving the moistening property, spreading property and lusterizing property of the cosmetic.

The cosmetic stick of the present invention comprises a water-in-oil emulsion comprising 1 to 50% by weight of water; a gel containing 1 to 10% by weight of at least one polyhydroxyl compound selected from the group consisting of glycerol, mannitol, dulcitol and carbohydrates and 1 to 5% by weight of at least one non-ionic surface active compound selected from the group consisting of oleic acid esters of polyhydric alcohols and oleyl ethers of polyhydric alcohols; and at least 20% by weight of at least one cosmetic base material.

The features of the present invention will be apparent from the following description and the accompanying drawing which shows rheological properties of a lipstick of the present invention and conventional lipsticks.

The cosmetic stick of the present invention includes a gel containing 1 to 10%, preferably, 5 to 7% by weight of at least one polyhydroxyl compound selected from the group consisting of glycerol, mannitol, dulcitol and carbohydrates and 1 to 5%, preferably, 2 to 3% by weight of at least one non-ionic surface active agent. The carbohydrate may be selected from D-levulose, maltose, sucrose, lactose, raffinose, starch, pentose, for example, D-ribose, D-xylose and L-arabinose, and hexose, for example, D-glucose, D-mannose and D-galactose. These carbohydrate compounds can be dissolved in water and gelatinized with the non-ionic surface active agent.

Furthermore, it should be noted that the above-specified polyhydroxyl compounds are essential for obtaining the water-in-oil type cosmetic stick containing coloring materials that are uniformly distributed and having a high resistance to mold. If sorbitol is used instead of the above-specified polyhydroxyl compounds, the resultant cosmetic stick has a non-uniform distribution of pigment therein and a low resistance to mold.

The cosmetic stick of the present invention includes at least one non-ionic surface active agent in an amount of 1 to 5%, preferably, 2 to 3% by weight. The surface active agent is selected from the group consisting of oleic acid esters of polyhydric alcohols and oleyl ethers of polyhydric alcohols. The oleic acid ester may be selected from glycerol monooleate, glycerol dioleate, sorbital monooleate, sorbitol sesquioleate, sorbitol trioleate, propylene glycol monooleate, propylene glycol dioleate, ethylene glycol monooleate, ethylene glycol dioleate and oleic acid esters of polyethylene glycols. Also, the non-ionic surface active oleyl ether may be selected from oleyl ethers of polyethylene glycols.

The polyhydroxyl compound is mixed with the non-ionic surface active agent to form a gel which is effective to stably emulsify the water in the cosmetic base material.

The cosmetic base material in the cosmetic stick of the present invention may be selected from liquid paraffins, squalane, castor oil, olive oil, avocado oil, camellia oil, cotton seed oil, almond oil, cocoa butter, sesame oil Japan wax, beeswax, lanolin, carnauba wax, candelilla wax, paraffin wax, solid paraffin, vaseline, (hereinafter also referred to as "petroleum jelly"), microcrystalline wax, and higher fatty acid esters. The liquid paraffin preferably has a viscosity of 50 to 365 saybolt second at 100°F. The higher hydrocarbons, for example, liquid paraffins and squalane may be mixed with about 20% of vegetable oil, for example, castor oil, olive oil, camellia oil; and higher fatty acid esters, for example, butyl stearate and iso-propyl myristate, and lanolin. The solid paraffin preferably has a melting point of 140° to 190°F and 20 or more carbon atoms, and contains 30 to 80% by weight of straight hydrocarbons.

The content of the cosmetic base material in the water-in-oil emulsion of the present invention is at least 20% by weight. If the content of the cosmetic base material is less than 20% by weight, it results in an unstable water-in-oil emulsion.

The cosmetic stick of the present invention may include organic coloring matters, for example, FD and C Red No. 3, DC Red No. 22, DC Red No. 28, FD and C Yellow No. 5, FD and C Yellow No. 6, FD and C Green No. 3, FD and C Blue No. 1, FD and C Blue No. 2, DC Red No. 6, DC Red No. 7, DC Red No. 9, DC Red No. 10, DC Red No. 11, DC Red No. 13, DC Red No. 21, DC Red No. 30, DC Orange No. 17, and DC Blue No. 6 and inorganic coloring material, for example, titanium dioxide, zinc white, talc, kaolin, iron oxide and carbon black. Further, the cosmetic stick of the present invention may contain one or more conventional additives for example, perfume, antioxidant, ultraviolet ray absorbing agent and germacide.

The water to be used in the cosmetic stick of the present invention is preferably microbially free deionized water.

The cosmetic stick of the present invention is prepared by the following procedure.

An aqueous solution of 1 to 10 parts, preferably, 5 to 7 parts by weight of the specified polyhydroxyl compound is mixed with 1 to 5 parts, preferably of 2 to 3 parts by weight of the specified non-ionic surface active agent to form a gel. The gel is mixed with a predetermined quantity of the cosmetic base material at a temperature of 50° – 60°C while stirring. Thereafter, water is mixed into the above-prepared cosmetic base material-gel mixture while stirring, whereby the water is uniformly emulsified into the cosmetic base material. The water mixed with the cosmetic base material-gel mixture is in the range from 1 to 50%, preferably, 10 to 20% by weight. More than 50% by weight of water results in high evaporation and low rigidity of the cosmetic stick. Less than 1% by weight of water is insufficient to provide a cosmetic stick capable of accomplishing the object of the present invention.

Less than 1% by weight of the non-ionic surface active agent is insufficient to provide a uniform gel, and more than 5% by weight thereof results in high irritation to human skin, discoloration of coloring matter and formation of numerous pin holes. If the polyhydroxyl compound is used in an amount of less than 1%, this results in non-uniform emulsification of water. Also, if the polyhydroxyl compound is in an amount of more than 10% by weight, this results in commercial disadvantage.

In the preparation of the conventional cosmetics, a relative large amount of surface active agent is used for emulsifying water into the hydrophobic cosmetic base material. The use of the large amount of surface active agent result in disadvantages of the resultant cosmetic stick namely, relatively high irritation to the human skin, high toxicity, discoloration of coloring matter, difficulty in control of hydrophile-lipophile balance (HLB) and formation of numerous pin holes due to bubbles produced in the cosmetic material. Especially, it is difficult to select the surface active agent having a suitable HLB for the combination of water and the cosmetic base material used.

In the method of preparation of the cosmetic stick of the present invention, the water is uniformly emulsified by using a relatively small amount, 1 to 5% by weight of the non-ionic surface active agent, because the surface active agent is preliminarily mixed with the polyhydroxyl compound which is highly hydrophilic and formed into a gel. The gel is effective for uniformly emulsifying water in the hydrophilic cosmetic base material.

In preparing the cosmetic stick of the present invention as described above, the water can contain at least one polyhydric alcohol selected from the group consisting of propolene glycol, 1,3-butylene glycol and dipropolene glycol.

The cosmetic stick of the present invention has the advantages as detailed below.
1. Property of spreading readily on human skin.
2. Property of providing good moisturization of the human skin.
3. Property of providing excellent luster to the human skin.
4. No irritation to the human skin due to small content of surface active agent.
5. Very little bleeding of the additive during prolonged storage.
6. Desirable soft feeling on human skin.
7. Excellent rigidity of the stick.
8. Excellent ability to accept addition of water-soluble non-toxic coloring matter and other additives.

Various embodiments of practicing the present invention are illustrated by the following examples.

These examples are intended merely to illustrate the present invention and not in any sense to limit the manner in which the present invention can be practiced. The parts percentage recited therein refer to parts by weight and percentages by weight.

EXAMPLE 1

Lipstick
(A) Cosmetic base (Oil parts)

| | |
|---|---|
| Liquid paraffin | 52.84 parts |
| Solid paraffin | 15.0 |
| Candelilla wax | 5.0 |
| TiO$_2$ | 5.70 |
| DC Red No. 7 | 1.30 |
| Butyl p-hydroxy benzoate | 0.05 |

The above-mentioned components were mixed uniformly at 80°C while agitating.

| (B) | Gel (Emulsifying agent) | | |
|---|---|---|---|
| | Glycerol monooleate | 3.0 | parts |
| | 60% aqueous solution of D-levulose | 2.0 | |
| (C) | Water parts | | |
| | Deionized water | 100 | parts |
| | Propylene glycol | 5.0 | |
| | FD and C Red No. 3 | 0.01 | |

The components were mixed at 35°C while stirring to form a gel.

The gel (B) thus prepared was mixed into the cosmetic base (A) at 70°C while stirring and then a mixture (C) composed of deionized water, propylene glycol and FD and C Red No. 3 was emulsified in the above mixture by stirring. The resultant composition was subjected to vacuum treatment to eliminate bubbles therein and poured into a lipstick mold. Uniform pink lipsticks with good luster were obtained.

For comparison, the same lipstick was prepared using sorbitol instead of the D-levulose. This lipstick had non-uniformity in distribution of TiO$_2$. That is, the TiO$_2$ was distributed in a larger concentration at the peripheral part than at the center part of the lipstick.

The lipstick of the present example was subjected to an accelerated storage (shelf-life) test. The lipstick was charged in a closed oven and the temperature of the oven was varied in cycle from 0°C to 38°C and then from 38°C to 0°C at intervals of 72 hours. After 3 months testing, no change was observed on the lipstick.

For comparison, two conventional lipsticks (a) and (b) were subjected to the same accelerated storage test as stated above. The conventional lipsticks (a) and (b) were of the following compositions

| Lipstick Component | (a) (part) | (b) (part) |
|---|---|---|
| Candelilla wax | 2 | 10 |
| Beeswax | — | 12 |
| Solid paraffin | 16 | — |
| Lanolin | 5 | — |
| Iso-propyl myristate | — | 15 |
| Castor oil | 34 | 56 |
| Camellia oil | 36 | — |
| Eosine | 0.01 | 0.01 |
| TiO$_2$ | 5.70 | 5.70 |
| DC Red: No. 7 | 1.29 | 1.29 |

After the accelerated storage (shelf-life) test for over one week, many perspiration-like particles of liquid were observed on the surface of the stick. This indicates that the liquid components were separated from the other components and bled out to the periphery of the lipsticks.

Further more the lipstick mass of the present example was subjected to a rheological measurement using a Ferranti-Shirley Cone and Plate Viscometer. The measurement was carried out in accordance with the method described in S. S. Davis, E. Shotton and B. Warburton, J. Pharm. Pharmacol 20, 157S–167S (1968), using a cone (model S) at 24°C, at a maximum rotation velocity of 100 r.p.m. of the cone for 10 seconds. The same rheological measurements as stated above were repeated for the mass of the conventional lipsticks (a) and (b). The results of the measurement are shown in the accompanying drawing. In the drawing, curve 1 shows a relationship between shear stress (I) and shear rate (D) of the lipstick of the present example, curve 2 the conventional lipstick (a) and curve 3 the conventional lipstick (b). As the drawing clearly shows, the yield stress of the lipstick mass of the present example is smaller than those of the conventional lipsticks (a) and (b). This shows that the lipstick mass of the present invention is desirably softer than the materials of the conventional lipsticks (a) and (b), and can be smoothly agitated at a small load even when the rotation velocity of the cone is increased.

The lipstick of the present example had the following advantages.
1. Butter-like soft touch to lips, and excellent compatibility to lips.
2. Excellent spreading property.
3. Excellent smoothness in application to lips.
4. Excellent lip moisturization property.
5. Elegance and high sheen.
6. High compatibility to inorganic coloring materials such as titanium dioxide, zinc white and iron oxide.
7. Excellent uniformity in color
8. Excellent stability over long storage.
9. Excellent resistance to breakage.
10. Excellent lip emollient property and property of providing excellent protection of lips from chapping.
11. High possibility of wide utilization of water-soluble dyes and edible coloring matter.

The conventional lipsticks (a) and (b) compared unfavorably with the lipstick of the present example in the properties as stated above.

EXAMPLE 2

| | Lippomade | | |
|---|---|---|---|
| (A) | Cosmetic base | | |
| | Liquid paraffin | 46.94 | parts |
| | Solid paraffin | 15.0 | |
| | Microcrystalline wax | 5.0 | |
| | Vaseline | 5.0 | |
| | Butyl-p-hydroxy benzoate | 0.05 | |
| (B) | Gel | | |
| | Sorbitol monooleate | 3.0 | |
| | Glycerol | 5.0 | |
| (C) | Deionized water | 15.0 | |
| | 1,3-butylene glycol | 5.0 | |
| | FD and C Yellow No. 5 | 0.01 | |

The same procedures as in Example 1 were repeated using the above composition and the composition was molded to form lippomades.

EXAMPLE 3

| | Cosmetique | | |
|---|---|---|---|
| (A) | Cosmetic base | | |
| | Liquid paraffin | 66.75 | parts |
| | Solid paraffin | 12.0 | |
| | Japan wax | 3.0 | |
| | Lanolin | 2.0 | |
| | Microcrystalline wax | 5.0 | |
| | Antioxidant | 0.2 | |
| | Butyl p-hydroxy benzoate | 0.05 | |
| (B) | Gel | | |
| | Sorbitol sesquioleate | 2.0 | |
| | 50% aqueous solution of D-glucose | 5.0 | |
| (C) | Deionized water | 2.0 | parts |
| | Propylene glycol | 1.0 | |
| | FD and C Yellow No. 5 | 1.0 | |

The same procedures as in Example 1 were repeated using the above composition and the composition was formed into cosmetiques by molding.

EXAMPLE 4

| | Stick foundation | | |
|---|---|---|---|
| (A) | Cosmetic base | | |
| | Liquid paraffin | 24.93 | parts |
| | Solid paraffin | 14.0 | |
| | Microcrystalline wax | 3.0 | |
| | Butyl p-hydroxybenzoate | 0.07 | |
| (B) | Gel | | |
| | Propylene glycol monooleate | 2.0 | parts |
| | Glycerol | 5.0 | |
| | Sorbitol monolaurate | 1.0 | |
| (C) | Deionized water | 25.0 | |
| | Propylene glycol | 5.0 | |
| | Zinc white and iron oxide (4:6) | 20.0 | |

The same procedures as in Example 1 were repeated using the above composition and the composition was molded to form stick foundations.

EXAMPLE 5

| | Lipstick | | |
|---|---|---|---|
| (A) | Cosmetic base | | |
| | Squalane | 16.92 | parts |
| | Solid paraffin | 15.0 | |
| | Carnauba wax | 2.0 | |
| | Butyl stearate | 3.0 | |
| | Butyl p-hydroxybenzoate | 0.05 | |
| (B) | Gel | | |
| | Sorbitol monooleate | 4.0 | |
| | 20% aqueous solution of D-mannitol | 7.0 | |
| (C) | Deionized water | 30.0 | |
| | Dipropylene glycol | 15.0 | |
| | Titanium dioxide | 5.70 | |
| | FD and C Red No. 9 | 1.30 | |
| | Methyl p-hydroxybenzoate | 0.03 | |

The same procedures as in Example I were repeated using the above composition and the composition was molded to form lipsticks.

EXAMPLE 6

| | Stick foundation | | |
|---|---|---|---|
| (A) | Cosmetic base | | |
| | Liquid paraffin | 16.93 | parts |
| | Squalane | 10.0 | |
| | Solid paraffin | 13.0 | |
| | Butyl p-hydroxybenzoate | 0.04 | |
| (B) | Gel | | |
| | Sorbitol sesquioleate | 3.0 | |
| | 40% aqueous solution of maltose | 7.0 | |
| (C) | Deionized water | 30.0 | |
| | 1,3-butylene glycol | 10.0 | |
| | Titanium dioxide and iron oxide (3 : 7) | 10.0 | |

-continued

| | | |
|---|---|---|
| Methyl p-hydroxybenzoate | 0.03 | |

The same procedures as in Example 1 were repeated using the above composition and the mass was molded to form stick foundations.

EXAMPLE 7

| | Cosmetique | | |
|---|---|---|---|
| (A) | Cosmetic base | | |
| | Liquid paraffin | 24.35 | parts |
| | Solid paraffin | 12.0 | |
| | Japan wax | 3.0 | |
| | Microcrystalline wax | 2.0 | |
| | Antioxidant | 0.2 | |
| | Butyl p-hydroxybenzoate | 0.05 | |
| (B) | Gel | | |
| | Glycerol dioleate | 2.0 | |
| | 50% aqueous solution of sucrose | 6.0 | |
| (C) | Deionized water | 40.0 | |
| | Dipropylene glycol | 10.0 | |
| | FD and Yellow No. 5 | 0.01 | |
| | Methyl p-hydroxybenzoate | 0.03 | |

The same procedures as in Example 1 were repeated using the above composition and the resultant water-in-oil emulsion mass was molded to form cosmetiques.

EXAMPLE 8

| | Lipstick | | |
|---|---|---|---|
| (A) | Cosmetic base | | |
| | Liquid paraffin | 42.98 | parts |
| | Squalane | 10.0 | |
| | Carnauba wax | 5.0 | |
| | Titanium dioxide | 3.86 | |
| | DC Orange No. 17 | 1.14 | |
| | Butyl p-hydroxybenzoate | 0.01 | |
| (B) | Gel | | |
| | Glycerol monooleate | 2.0 | |
| | Sorbitol monooleate | 2.0 | |
| | 50% aqueous solution of sucrose | 5.0 | |
| | Glycerol | 3.0 | |
| (C) | Deionized water | 15.0 | |
| | 1,3-butylene glycol | 10.0 | |
| | FD and C Yellow No. 6 | 0.01 | |

The same procedures as in Example 1 were repeated using the above composition, the resultant water-in-oil emulsion mass was molded to form lipsticks.

EXAMPLE 9

| | Lipstick | | |
|---|---|---|---|
| (A) | Cosmetic base | | |
| | Solid paraffin | 37.94 | parts |
| | Liquid paraffin | 20.0 | |
| | Microcrystalline wax | 10.0 | |
| | Titanium dioxide | 2.10 | |
| | DC Red No. 10 | 4.90 | |
| | Butyl p-hydroxybenzoate | 0.05 | |
| (B) | Gel | | |
| | Sorbitol sesquioleate | 3.0 | |
| | 60% aqueous solution of D-levulose | 4.0 | |
| | 50% aqueous solution of sucrose | 3.0 | |
| (C) | Deionized water | 10.0 | |
| | Propylene glycol | 5.0 | |
| | DC Red No. 28 | 0.01 | |

The same procedures as in Example 1 were repeated using the above composition and the resulting water-in-oil emulsion mass was molded to form lipsticks.

EXAMPLE 10

| | Cosmetique | | |
|---|---|---|---|
| (A) | Cosmetic base | | |

-continued

| | | | |
|---|---|---|---|
| | Liquid paraffin | 16.21 | parts |
| | Solid paraffin | 15.0 | |
| | Japan wax | 5.0 | |
| | Candelilla wax | 2.0 | |
| | Antioxidant | 0.2 | |
| | Butyl p-hydroxybenzoate | 0.05 | |
| (B) | Gel | | |
| | Glycerol monooleate | 2.0 | |
| | Sorbitol sesquioleate | 1.0 | |
| | 20% aqueous solution of D-mannitol | 2.5 | |
| | Glycerol | 6.0 | |
| (C) | Deionized water | 40.0 | |
| | Dipropylene glycol | 10.0 | |
| | FD and C Blue No. 1 | 0.01 | |
| | Methyl p-hydroxybenzoate | 0.03 | |

The same procedures as in Example 1 were repeated using the above composition, the resultant water-in-oil emulsion mass was molded to form cosmetiques.

The cosmetique thus prepared was subjected to a mold culture test at a temperature of 25°C at a relative humidity of 80% over two weeks. No mold was observed on the cosmetique of the present example.

For comparison, a cosmetique was prepared using sorbitol instead of glycerol. The comparison cosmetique was subjected to the same mold culture test as that stated above. After incubating for two weeks, mold was clearly observed on the comparison lipstick cosmetique.

What we claim is:

1. A process for making a water-in-oil cosmetic stick which comprises:
   a. preparing a gel by mixing an aqueous solution of 1 to 10% by weight of at least one polyhydroxl compound selected from the group consisting of glycerol, mannitol and carbohydrates and 1 to 5% by weight of at least one non-ionic surface active agent selected from oleic acid esters of polyhydric alcohols;
   b. mixing said gel with a predetermined quantity of at least 20% by weight of at least one cosmetic base material; and
   c. mixing from 1 to 50% by weight of water into said cosmetic base material-gel mixture whereby the water is uniformly emulsified into said mixture.

2. A cosmetic stick prepared by the process of claim 1.

3. A process for making a cosmetic stick as claimed in claim 1, wherein said non-ionic surface active oleic acid ester of polyhydric alcohol is selected from the group consisting of glycerol monooleate, glycerol dioleate, glycerol trioleate, sorbitol monooleate, sorbitol sesquioleate, sorbitol trioleate, propylene glycol monooleate, propylene glycol dioleate, ethylene glycol monooleate and ethylene glycol dioleate.

4. A cosmetic stick prepared by the process of claim 3.

5. A process for making a cosmetic stick as claimed in claim 1, wherein said cosmetic base material contains an ingredient selected from the group consisting of liquid paraffins, squalene, castor oil, olive oil, avocado oil, camellia oil, cottonseed oil, almond oil, cocoa butter, sesame oil, Japan wax, beeswax, lanolin, carnauba wax, candelilla wax, paraffin waxes, ceresin, petroleum jelly and microcrystalline wax.

6. A cosmetic stick prepared by the process of claim 5.

7. A process for making a cosmetic stick as claimed in claim 1, wherein said water is in an amount of 10 to 20% by weight.

8. A cosmetic stick prepared by the process of claim 7.

9. A process for making a cosmetic stick as claimed in claim 1, wherein said polyhydroxyl compound is in an amount of 5 to 7% by weight.

10. A cosmetic stick prepared by the process of claim 9.

11. A process for making a cosmetic stick as claimed in claim 1, wherein said non-ionic surface active agent is in an amount of 2 to 3% by weight.

12. A cosmetic stick prepared by the process of claim 11.

13. A process for making a cosmetic stick as claimed in claim 1, wherein said carbohydrate is selected from the group consisting of D-levulose, maltose, sucrose, lactose, raffinose, D-ribose, D-xylose, L-arabinose, D-glucose, D-mannose, D-galactose and starch.

14. A cosmetic stick prepared by the process of claim 13.

* * * * *